United States Patent
Griffith

(10) Patent No.: US 9,446,242 B2
(45) Date of Patent: Sep. 20, 2016

(54) SYSTEM AND METHOD FOR INDEPENDENTLY OPERATING MULTIPLE NEUROSTIMULATION CHANNELS

(71) Applicant: Boston Scientific Neuromodulation Corporation, Valencia, CA (US)

(72) Inventor: Paul James Griffith, Moorpark, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/813,468

(22) Filed: Jul. 30, 2015

(65) Prior Publication Data

US 2015/0328462 A1 Nov. 19, 2015

Related U.S. Application Data

(63) Continuation of application No. 14/082,732, filed on Nov. 18, 2013, now Pat. No. 9,095,714, which is a continuation of application No. 12/976,223, filed on Dec. 22, 2010, now Pat. No. 8,615,306.

(60) Provisional application No. 61/291,058, filed on Dec. 30, 2009.

(51) Int. Cl.
*A61N 1/36* (2006.01)
*A61N 1/05* (2006.01)

(52) U.S. Cl.
CPC ......... *A61N 1/36125* (2013.01); *A61N 1/0531* (2013.01); *A61N 1/0534* (2013.01); *A61N 1/36082* (2013.01); *A61N 1/36182* (2013.01); *A61N 1/36071* (2013.01)

(58) Field of Classification Search
CPC .. A61N 1/36; A61N 1/3605; A61N 1/36021; A61N 1/36003; A61N 1/0551
USPC ................ 607/2, 45–46, 48, 66, 72, 74, 117
See application file for complete search history.

(56) References Cited

U.S. PATENT DOCUMENTS 5,562,718 A 10/1996 Palermo
6,845,267 B2 1/2005 Harrison et al.

(Continued)

FOREIGN PATENT DOCUMENTS

WO WO-2011/082071 A1 7/2011

OTHER PUBLICATIONS

"U.S. Appl. No. 12/976,223, Final Office Action mailed Dec. 19, 2012", 9 pgs.

(Continued)

*Primary Examiner* — Catherine Voorhees
*Assistant Examiner* — Roland Dinga
(74) *Attorney, Agent, or Firm* — Schwegman Lundberg & Woessner, P.A.

(57) ABSTRACT

A multi-channel neurostimulation system comprises a plurality of electrical terminals configured for being respectively coupled to a plurality of electrodes, stimulation output circuitry including electrical source circuitry of the same polarity configured for generating a plurality of pulsed electrical waveforms in a plurality of timing channels, and control circuitry configured for instructing the stimulation output circuitry to serially couple the electrical source circuitry to different sets of the electrodes when pulses of the respective pulsed electrical waveforms do not temporally overlap each other, and for instructing the stimulation output circuitry to couple the electrical source circuitry to a union of the different electrode sets when pulses of the respective pulsed electrical waveforms temporally overlap each other.

20 Claims, 13 Drawing Sheets

(56) References Cited

U.S. PATENT DOCUMENTS

| | | | |
|---|---|---|---|
| 6,895,280 B2 | 5/2005 | Meadows et al. | |
| 6,950,707 B2 | 9/2005 | Whitehurst | |
| 7,254,445 B2 | 8/2007 | Law et al. | |
| 7,353,064 B2 | 4/2008 | Gliner et al. | |
| 8,615,306 B2 | 12/2013 | Griffith | |
| 9,095,714 B2 | 8/2015 | Griffith | |
| 2006/0020306 A1* | 1/2006 | Davis | A61N 1/3787 607/61 |
| 2007/0073356 A1 | 3/2007 | Rooney et al. | |
| 2007/0100399 A1 | 5/2007 | Parramon et al. | |
| 2007/0213783 A1 | 9/2007 | Pless | |
| 2007/0293914 A1* | 12/2007 | Woods | A61N 1/36071 607/60 |
| 2008/0208287 A1 | 8/2008 | Palermo et al. | |
| 2010/0331916 A1 | 12/2010 | Parramon et al. | |
| 2011/0054567 A1* | 3/2011 | Lane | A61N 1/08 607/59 |
| 2011/0054568 A1 | 3/2011 | Lane et al. | |
| 2011/0054570 A1 | 3/2011 | Lane | |
| 2014/0074190 A1 | 3/2014 | Griffith | |

OTHER PUBLICATIONS

"U.S. Appl. No. 12/976,223, Non Final Office Action mailed Feb. 28, 2013", 10 pgs.

"U.S. Appl. No. 12/976,223, Non Final Office Action mailed Apr. 24, 2012", 11 pgs.

"U.S. Appl. No. 12/976,223, Notice of Allowance mailed Aug. 26, 2013", 8 pgs.

"U.S. Appl. No. 12/976,223, Response filed Jan. 23, 2013 to Final Office Action mailed Dec. 19, 2012", 5 pgs.

"U.S. Appl. No. 12/976,223, Response filed May 20, 2013 to Non Final Office Action mailed Feb. 28, 2013", 5 pgs.

"U.S. Appl. No. 12/976,223, Response filed Jul. 18, 2012 to Non Final Office Action mailed Apr. 24, 2012", 4 pgs.

"U.S. Appl. No. 14/082,732, Final Office Action mailed Feb. 17, 2015", 8 pgs.

"U.S. Appl. No. 14/082,732, Non Final Office Action mailed Oct. 23, 2014", 9 pgs.

"U.S. Appl. No. 14/082,732, Notice of Allowance mailed Mar. 24, 2015", 5 pgs.

"U.S. Appl. No. 14/082,732, Preliminary Amendment filed Jan, 23, 2014", 5 pgs.

"U.S. Appl. No. 14/082,732, Response filed Jan. 21, 2015 to Non Final Office Action mailed Oct. 23, 2014", 6 pgs.

"U.S. Appl. No. 14/082,732, Response filed Mar. 5, 2015 to Final Office Action mailed Feb. 17, 2015", 5 pgs.

"Australian Application Serial No. 2010336976, Amendment filed Jun. 28, 2012", 11 pgs.

"European Application Serial No. 10801776.5, Office Action mailed Aug. 31, 2012", 2 pgs.

"European Application Serial No. 10801776.5, Response filed Mar. 10, 2013 to Office Action mailed Aug. 31, 2012", 9 pgs.

"International Application Serial No. PCT/US2010/061839, International Preliminary Report on Patentability mailed Jul. 12, 2012", 8 pgs.

"International Application Serial No. PCT/US2010/061839, International Search Report mailed Jun. 8, 2011", 5 pgs.

"International Application Serial No. PCT/US2010/061839, Written Opinion mailed Jun. 8, 2011", 6 pgs.

"Japanese Application Serial No. 2012-547156, Amendment filed Jan. 13, 2015", English Claims, 4 pgs.

"Japanese Application Serial No. 2012-547156, Office Action mailed Sep. 1, 2014", With Partial English Translation, 3 pgs.

Alessandro, Stefani, et al., "Bilateral deep brain stimulation of the pedunculopntine and subthalamic nuclei in severe Parkinson's disease", Brain, 130, (2007), 1596-1607.

Birno, M. J, et al., "Pulse-to-Pulse Changes in the Frequency of Deep Brain Stimulation Affect Tremor and Modeled Neuronal Activity", J. Neurophysiol. 98, (2007), 1675-1684.

\* cited by examiner

TIMING CHANNEL 1

| ELECTRODE# | COARSE BRANCH# | FINE BRANCH# | POLARITY |
|---|---|---|---|
| GLOBAL AMPLITUDE | 10000000 | | |
| E1 | 00100 | 100 | 0 |
| E2 | 00000 | 000 | 0 |
| E3 | 00100 | 100 | 1 |
| E4 | 00000 | 000 | 0 |
| E5 | 00000 | 000 | 0 |
| E6 | 00000 | 000 | 0 |
| E7 | 00000 | 000 | 0 |
| E8 | 00000 | 000 | 0 |
| E9 | 00000 | 000 | 0 |
| E10 | 00000 | 000 | 0 |
| E11 | 00000 | 000 | 0 |
| E12 | 00000 | 000 | 0 |
| E13 | 00000 | 000 | 0 |
| E14 | 00000 | 000 | 0 |
| E15 | 00000 | 000 | 0 |
| E16 | 00000 | 000 | 0 |
| Ecase | 00000 | 000 | 0 |

FIG. 12a

TIMING CHANNEL 2

| ELECTRODE# | COARSE BRANCH# | FINE BRANCH# | POLARITY |
|---|---|---|---|
| GLOBAL AMPLITUDE | 10000000 | | |
| E1 | 00000 | 000 | 0 |
| E2 | 00000 | 000 | 0 |
| E3 | 00000 | 000 | 0 |
| E4 | 00000 | 000 | 0 |
| E5 | 00000 | 000 | 0 |
| E6 | 00000 | 000 | 0 |
| E7 | 00000 | 000 | 0 |
| E8 | 00000 | 000 | 0 |
| E9 | 00000 | 000 | 0 |
| E10 | 00000 | 000 | 0 |
| E11 | 00000 | 000 | 0 |
| E12 | 00000 | 000 | 0 |
| E13 | 00100 | 100 | 0 |
| E14 | 00100 | 100 | 1 |
| E15 | 00000 | 000 | 0 |
| E16 | 00000 | 000 | 0 |
| Ecase | 00000 | 000 | 0 |

FIG. 12b

TIMING CHANNEL 3
GLOBAL AMPLITUDE   10000000

| ELECTRODE# | COARSE BRANCH# | FINE BRANCH# | POLARITY |
|---|---|---|---|
| E1 | 00000 | 000 | 0 |
| E2 | 00000 | 000 | 0 |
| E3 | 00000 | 000 | 0 |
| E4 | 00000 | 000 | 0 |
| E5 | 00000 | 000 | 0 |
| E6 | 00100 | 100 | 0 |
| E7 | 00010 | 010 | 0 |
| E8 | 00111 | 001 | 1 |
| E9 | 00000 | 000 | 0 |
| E10 | 00000 | 000 | 0 |
| E11 | 00000 | 000 | 0 |
| E12 | 00000 | 000 | 0 |
| E13 | 00000 | 000 | 0 |
| E14 | 00000 | 000 | 0 |
| E15 | 00000 | 000 | 0 |
| E16 | 00000 | 000 | 0 |
| Ecase | 00000 | 000 | 0 |

FIG. 12c

TIMING CHANNEL 4
GLOBAL AMPLITUDE   10000000

| ELECTRODE# | COARSE BRANCH# | FINE BRANCH# | POLARITY |
|---|---|---|---|
| E1 | 00000 | 000 | 0 |
| E2 | 00000 | 000 | 0 |
| E3 | 00000 | 000 | 0 |
| E4 | 00000 | 000 | 0 |
| E5 | 00000 | 000 | 0 |
| E6 | 00000 | 000 | 0 |
| E7 | 00000 | 000 | 0 |
| E8 | 00110 | 000 | 1 |
| E9 | 00000 | 000 | 0 |
| E10 | 00110 | 000 | 0 |
| E11 | 00000 | 000 | 0 |
| E12 | 00000 | 000 | 0 |
| E13 | 00000 | 000 | 0 |
| E14 | 00000 | 000 | 0 |
| E15 | 00000 | 000 | 0 |
| E16 | 00000 | 000 | 0 |
| Ecase | 00000 | 000 | 0 |

FIG. 12d

Union of TIMING CHANNELS 1 and 2
GLOBAL AMPLITUDE   10000000

| ELECTRODE# | COARSE BRANCH# | FINE BRANCH# | POLARITY |
|---|---|---|---|
| E1 | 00100 | 100 | 0 |
| E2 | 00000 | 000 | 0 |
| E3 | 00100 | 100 | 1 |
| E4 | 00000 | 000 | 0 |
| E5 | 00000 | 000 | 0 |
| E6 | 00000 | 000 | 0 |
| E7 | 00000 | 000 | 0 |
| E8 | 00000 | 000 | 0 |
| E9 | 00000 | 000 | 0 |
| E10 | 00000 | 000 | 0 |
| E11 | 00000 | 000 | 0 |
| E12 | 00000 | 000 | 0 |
| E13 | 00100 | 100 | 0 |
| E14 | 00100 | 100 | 1 |
| E15 | 00000 | 000 | 0 |
| E16 | 00000 | 000 | 0 |
| Ecase | 00000 | 000 | 0 |

FIG. 13

SYSTEM AND METHOD FOR INDEPENDENTLY OPERATING MULTIPLE NEUROSTIMULATION CHANNELS

RELATED APPLICATION

The present application is a continuation of U.S. patent application Ser. No. 14/082,732, filed Nov. 18, 2013, now issued as U.S. Pat. No. 9,095,714, which is a continuation of U.S. patent application Ser. No. 12/976,223, filed Dec. 22, 2010, now issued as U.S. Pat. No. 8,615,306, which claims the benefit under 35 U.S.C. §119 to U.S. provisional patent application Ser. No. 61/291,058, filed Dec. 30, 2009. The foregoing applications are hereby incorporated by reference into the present application in their entirety.

FIELD OF THE INVENTION

The present invention relates to tissue stimulation systems, and more particularly, to a system and method for operating multiple neurostimulation channels.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence.

More pertinent to the present inventions described herein, Deep Brain Stimulation (DBS) has been applied therapeutically for well over a decade for the treatment of neurological disorders. DBS and other related procedures involving implantation of electrical stimulation leads within the brain of a patient are increasingly used to treat disorders, such as Parkinson's disease, essential tremor, seizure disorders, obesity, depression, obsessive-compulsive disorder, Tourette's syndrome dystonia, and other debilitating diseases via electrical stimulation of one or more target sites, including the ventrolateral thalamus, internal segment of globus pallidus, substantia nigra pars reticulate, subthalamic nucleus (STN), or external segment of globus pallidus.

DBS has become a prominent treatment option for many disorders, because it is a safe, reversible alternative to lesioning. For example, DBS is the most frequently performed surgical disorder for the treatment of advanced Parkinson's Disease. There have been approximately 30,000 patients world-wide that have undergone DBS surgery. Consequently, there is a large population of patients who will benefit from advances in DBS treatment options. Further details discussing the treatment of diseases using DBS are disclosed in U.S. Pat. Nos. 6,845,267 and 6,950,707, which are expressly incorporated herein by reference.

Implantable neurostimulation systems typically include one or more electrode carrying stimulation leads, which are implanted at the desired stimulation site, and a neurostimulator (e.g., an implantable pulse generator (IPG)) implanted remotely from the stimulation site, but coupled either directly to the stimulation lead(s) or indirectly to the stimulation lead(s) via a lead extension. The neurostimulation system may further comprise an external control device to remotely instruct the neurostimulator to generate electrical stimulation pulses in accordance with selected stimulation parameters.

Electrical stimulation energy may be delivered from the neurostimulator to the electrodes in the form of a pulsed electrical waveform. Thus, stimulation energy may be controllably delivered to the electrodes to stimulate neural tissue. The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include the amplitude, duration, and frequency of the electrical pulses provided through the electrode array. Each electrode combination, along with the electrical pulse parameters, can be referred to as a "stimulation parameter set."

With some neurostimulation systems, and in particular, those with independently controlled current or voltage sources, the distribution of the current to the electrodes (including the case of the neurostimulator, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode configurations).

In the context of DBS, a multitude of brain regions may need to be electrically stimulated in order to treat one or more ailments associated with these brain regions. To this end, multiple stimulation leads are typically implanted adjacent the multiple brain regions. In particular, multiple burr holes are cut through the patient's cranium as not to damage the brain tissue below, a large stereotactic targeting apparatus is mounted to the patient's cranium, and a cannula is scrupulously positioned through each burr hole one at a time towards each target site in the brain. Microelectrode recordings may typically be made to determine if each trajectory passes through the desired part of the brain, and if so, the stimulation leads are then introduced through the cannula, through the burr holes, and along the trajectories into the parenchyma of the brain, such that the electrodes located on the lead are strategically placed at the target sites in the brain of the patient.

Stimulation of multiple brain structures (i.e., different functional regions of the brain) with different sets of stimulation parameters has been shown to be useful. For example, stimulation of the Pedunculopontine (PPN) and Subthalamic Nuclei (STN) at different frequencies has been shown to be beneficial (see Alessandro Stefani, et al. "Bilateral Deep Brain Stimulation of the Pedunculopontine and Subthalamic Nuclei in Severe Parkinson's Disease," Brain (2007); 130 1596-1607). In another DBS example, one frequency is used to optimize treatment of tremor and rigidity, while another frequency is used to treat bradykinesia (see U.S. Pat. No. 7,353,064).

Thus, if the same set of stimulation parameters is used to stimulate the different brain structures, either (1) one brain structure may receive optimal therapy and the other brain structure may receive poor therapy, or, (2) both brain structures may receive mediocre therapy. Thus, to maximize the therapeutic effects of DBS, each brain structure may require different sets of stimulation parameters (i.e. different amplitudes, different durations, and/or frequencies).

One way that prior art DBS techniques attempt to stimulate several brain structures using different stimulation parameters is to implant multiple leads adjacent the different regions of the brain, and to quickly cycle the stimulation through the brain structures with the different stimulation parameters. In some applications, such as the treatment of chronic pain, this effect may be unnoticeable; however, the brain is a complex system of rapidly transmitting electric signals, and the effect of rapid cycling may produce a "helicopter effect" that may undesirably result in ineffective treatment and/or side-effects such as seizures.

Another way that prior art DBS techniques attempt to stimulate several brain structures using different stimulation parameters is to connect the multiple leads to multiple neurostimulators respectively programmed with different stimulation parameters. However, this increases the cost of the procedure, increases the length of the procedure, and increases the risks associated with the surgery.

Another approach is to use multiple timing channels when applying electrical stimulation to different brain structures. Each timing channel identifies the combination of electrodes used to deliver electrical pulses to the targeted tissue, as well as the characteristics of the current (pulse amplitude, pulse duration, pulse frequency, etc.) flowing through the electrodes. Because prior art neurostimulation systems are incapable of simultaneously controlling the generation of electrical pulses (e.g., either because they comprise only one anodic electrical source and one cathodic electrical source or otherwise because one or more stimulation parameters used to define one electrical pulse may be overwritten with one or more stimulation parameters used to define a subsequent overlapping electrical pulse), the use of multiple timing channels can often lead to issues due to the potential of an overlap in electrical pulses between two or more timing channels. These neurostimulation systems may time-multiplex the pulsed electrical waveforms generated in each of the multiple channels to prevent electrical pulses in the respective channels from overlapping each other.

For example, with reference to FIG. 1, one prior art neurostimulation controller 1 that is capable of controlling output stimulation circuitry 2 to output up to four pulsed electrical waveforms respectively over four timing channels in accordance with four stimulation parameter sets. The output stimulation circuitry 2 includes a single anodic current source 3a and an associated decoder 4a (or bank of decoders), and a single cathodic current source 3b and an associated decoder 4b (or bank of decoders). The decoder 4a is configured for decoding a digital code defining an anodic electrode combination (i.e., the active anodic electrodes) and amplitude values for the anodic electrode combination, and the decoder 4b is configured for decoding a digital code defining a cathodic electrode combination (i.e., the active cathodic electrodes) and amplitude values for the cathodic electrode combination.

The neurostimulation controller 1 comprises a number of registers 5 (in this case, four registers 1-4), each of which digitally stores certain parameters of one of the four stimulation parameter sets, and in particular, the electrode combination (i.e., the active electrodes) and amplitude and polarity (cathode or anode) of each of the active ones of the electrode combination. The neurostimulation controller 1 further comprises a number of timers 6 (in this case, four timers 1-4), each of which controls the pulse duration and frequency of one of the four stimulation parameter sets by outputting a high/low signal.

The neurostimulation controller 1 further comprises a multiplexor/selector 7 that outputs the digital contents (electrode combination, amplitude, and polarity) of a selected one of the registers 5 to the decoders 3 of the stimulation output circuitry 1 when the signal output by the respective timer 6 to the multiplexor/selector 7 is high (i.e., a logical 1 on one of the timers 6 gates the associated register 5 to the output of the multiplexor/selector 7). The stimulation output circuitry 2 then outputs an anodic electrical pulse and a cathodic electrical pulse in accordance with the electrode combination, amplitude, and polarity defined by the digital contents of the respective register 5 and decoded by the decoders 3, and the pulse width and frequency defined by the respective timer 6.

The neurostimulation controller 1 further comprises an arbitrator 8 for serially selecting the timing channels in which anodic and cathodic pulses will be output by the stimulation output circuitry 2 by serially turning on the timers 6, and thus, serially outputting the digital contents of the respective register 5 to the stimulation output circuitry 5. The arbitrator 8 selects the timing channels in a manner that prevents overlap of electrical pulses between the channels to avoid the aforementioned problems associated with attempting to generate overlapping pulses using single-source output circuitry. Notably, for the specific architecture illustrated in FIG. 1, preventing overlap of electrical pulses will ensure that information of a current electrical pulse (i.e., the digital contents obtained from one of the registers 5) stored within the decoders 3 of the stimulation output circuitry 2 is not overwritten with information of an overlapping electrical pulse (i.e., the digital contents obtained from another of the registers 5) when subsequently stored in the decoders 3 of the stimulation output circuitry 2.

If the frequencies of two pulsed electrical waveforms are the same or a harmonic of the other, the electrical pulses can be easily spaced in time within the respective channels, such that they do not coincide, as illustrated by the pulsed electrical waveforms in FIG. 2. For purposes of simplicity, only the anodic portion of the pulsed electrical waveforms is shown. When the frequencies of two pulsed electrical waveforms are not the same or otherwise not a harmonic of each other, the pulses of the pulsed electrical waveform with the faster frequency will "walk" over the pulses in the other pulsed electrical waveform, and therefore, there will be occasions when the pulses in the respective channels will need to be simultaneously generated, as illustrated in FIG. 3.

However, when there is only one source for each polarity, as shown in FIG. 1, or at least, when there are one or more non-dedicated sources (i.e., a source that can be shared by multiple electrodes), two electrical pulses of the same polarity cannot be generated simultaneously due to the potential of digitally overwriting the electrode combination information of the first electrical pulse with the electrode combination information associated with the second electrical pulse. Thus, even though multiple pulsed electrical waveforms can be generated in multiple channels, they must all have related frequencies to maintain a constant period, unless at least one pulsed electrical waveform is modified.

For example, in one embodiment, the arbitrator 8 uses a method known as the "token" method to prevent overlap of stimulation pulses between channels by modifying one or more of the pulsed electrical waveforms. This method allows an electrical pulse to be transmitted in the timing channel with the "token," while the other timing channels wait their turn. Then, the "token" is passed to the next timing channel. However, if the channels overlap, such that they need the "token" at the same time, transmission of an electrical pulse within the second channel must wait until the end of the transmission of the electrical pulse in the first timing channel. The arbitrator 8 accomplishes this by putting the timer 6 associated with the subsequent electrical pulse on hold while the output of the multiplexor/selector 7 is in use.

The "token" method may best be understood with reference to FIG. 4. As there shown, a first pulsed electrical waveform 9a having a first frequency is transmitted within timing channel A, and a second pulsed electrical waveform 9b having a second frequency is desired to be transmitted within timing channel B. Because timing channel A has the "token," the pulses of the second pulsed electrical waveform 9b that are to be transmitted in timing channel B must be "bumped" each time they overlap with the pulses of the first pulsed electrical waveform 9a. As can be seen in the bumped pulsed electrical waveform 9c, when a pulse is bumped (shown by the horizontal arrows), the next pulse relies on the new (bumped) pulse for timing. Thus, the next pulse is "double bumped": once when the previous pulse is bumped and a second time when it overlaps a pulse of the pulsed electrical waveform 9a transmitted in the timing channel A. As a result, the frequency of the pulses in the second pulsed electrical waveform 9b is forced (i.e., locked) into the frequency for the first pulsed electrical waveform 9a, resulting in a pulsed electrical waveform 9d that has a frequency twice as small as the desired frequency.

One adverse result of using the token method is that the frequency of the electrical pulses transmitted in the second timing channel gets "locked" to (i.e. matches) the frequency of the electrical pulses transmitted in the first timing channel; alternatively, one can get galloping or clumping of electrical pulses. Therefore, when the occurrence of electrical pulses is pushed out in time, stimulation therapy may become ineffective or even harmful for tissue regions, such as brain structures to be stimulated in DBS applications, that require stimulation at specific, regular frequencies (See Birno M J, Cooper S E, Rezai A R, Grill W M, Pulse-to-Pulse Changes in the Frequency of Deep Brain Stimulation Affect Tremor and Modeled Neuronal Activity, J. Neurophysiology, 2007 September; 98(3): 1675-84.

There, thus, remains a need to provide an improved technique for independently operating multiple stimulation channels in a neurostimulation system where at least one electrical source in the neurostimulation system is shared by a plurality of electrodes.

SUMMARY OF THE INVENTION

In accordance with one aspect of the present inventions, a multi-channel neurostimulation system is provided. The neurostimulation system comprises a plurality of electrical terminals configured for being respectively coupled to a plurality of electrodes, and stimulation output circuitry including electrical source circuitry of the same polarity configured for generating a plurality of pulsed electrical waveforms in a plurality of timing channels. The pulsed electrical waveforms may have different pulse frequencies. In one embodiment, the stimulation output circuitry includes at least one switch bank coupled between the electrical source circuitry and the electrical terminals.

The neurostimulation system further comprises control circuitry configured for instructing the stimulation output circuitry to serially couple the electrical source circuitry to different sets of the electrodes when pulses of the respective pulsed electrical waveforms do not temporally overlap each other, and for instructing the stimulation output circuitry to couple the electrical source circuitry to a union of the different electrode sets when pulses of the respective pulsed electrical waveforms temporally overlap each other.

The neurostimulation system may further comprise a housing containing the plurality of electrical terminals, stimulation output circuitry, and control circuitry. Alternatively, some of the components of the neurostimulation system may be contained in separate housings. In one embodiment, the electrical source circuitry comprises a current source. In this case, electrical source circuitry may comprise a plurality of current branches, and the control circuitry may be configured for selecting a current magnitude for each electrode in the union of the different electrode sets by assigning one or more of the current branches to the respective electrode.

In another embodiment, the pulsed electrical waveforms are defined by a respective plurality of stimulation parameter sets, in which case, the control circuitry is configured for obtaining a digital representation of an electrode set from each of the stimulation parameter sets, combining the digital representations together to create a union of the digital representations, and outputting the digital representation union to the stimulation circuitry, and the stimulation output circuitry is configured for coupling the electrical source circuitry to the union of the different electrode sets in accordance with the digital representation union. Each of the digital representations may comprise a digital representation of current amplitude values for the respective electrode set, in which case, the control circuitry may be configured for instructing the stimulation output circuitry to supply electrical current from the electrical source circuitry to the different sets of the electrodes or the union of the different electrode sets in accordance with the current amplitude values.

In still another embodiment, the control circuitry includes a plurality of registers configured for storing digital representations of the electrode sets, and a plurality of timers configuring for outputting phase enabling signals in accordance with a pulse duration and frequency of the pulsed electrical waveforms. The phase enabling signal output by each of the timers may, e.g., be high when the pulse of the respective pulsed electrical waveform is active. The control circuitry may further include a plurality of AND gates, each of which has an input coupled to an output of a respective one of the registers and an input coupled to an output of a respective one of the timers, and an OR gate having inputs coupled to respective outputs of the AND gates, and an coupled to an input of the stimulation output circuitry.

In accordance with a second aspect of the present inventions, another multi-channel neurostimulation system is provided. The neurostimulation system comprises a plurality of electrical terminals configured for being respectively coupled to a plurality of electrodes, a plurality of registers configured for storing a respective plurality of digital representations of different sets of the electrodes, and a plurality of timers configuring for outputting phase enabling signals in accordance with a pulse duration and pulse frequency of a respective plurality of pulsed electrical waveforms. The pulsed electrical waveforms may have different pulse frequencies. In one embodiment, the timers are operated independently of each other.

The neurostimulation system further comprises a plurality of AND gates, each of which has an input coupled to an output of a respective one of the registers and an input coupled to an output of a respective one of the timers, and an OR gate having inputs coupled to respective outputs of the AND gates.

The neurostimulation system further comprises stimulation output circuitry having an input coupled to an output of the OR gate. The stimulation output circuitry includes electrical source circuitry of the same polarity programmable to selectively couple to the electrodes via the electrical terminals based on the output of the OR gate. The neurostimulation system may further comprise a housing containing the plurality of electrical terminals, the plurality of registers, the plurality of timers, the plurality of AND gates, the OR gate, and the stimulation output circuitry. Alternatively, some of the components of the neurostimulation system may be contained in separate housings.

In one embodiment, the electrical source circuitry comprises a current source. In this case, each of the digital representations may comprise a digital representation of current amplitude values for the respective electrode set, and the electrical source circuitry may be programmable to supply current to the electrodes based on the output of the OR gate. The electrical source circuitry may comprise a plurality of current branches, in which case, the neurostimulation system may further comprise a branch distribution circuit configured for assigning one or more of the current branches to each of the electrodes based on the output of the OR gate. Each current branch may comprise a switch bank coupled to the electrodes, and a decoder coupled to the respective switch bank, wherein the branch distribution circuit is configured for supplying a digital code to each of the decoders, and the digital code defines one of the electrodes to be coupled to the electrical source circuitry via the respective switch bank.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIGS. 12a-12d illustrate digital representations of active electrodes, electrode polarity, and amplitude values for timing channels 1-4 stored in registers of the control circuitry of FIG. 11; and FIG. 13 illustrates a union of the digital representations illustrated in FIGS. 12a and 12b for timing channels 1 and 2.

DETAILED DESCRIPTION OF THE EMBODIMENTS

The description that follows relates to a deep brain stimulation (DBS) system. However, it is to be understood that the while the invention lends itself well to applications in DBS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a spinal cord stimulator, peripheral nerve stimulator, microstimulator, or in any other neural stimulator configured to treat urinary incontinence, sleep apnea, shoulder sublaxation, headache, etc.

Figure 1:
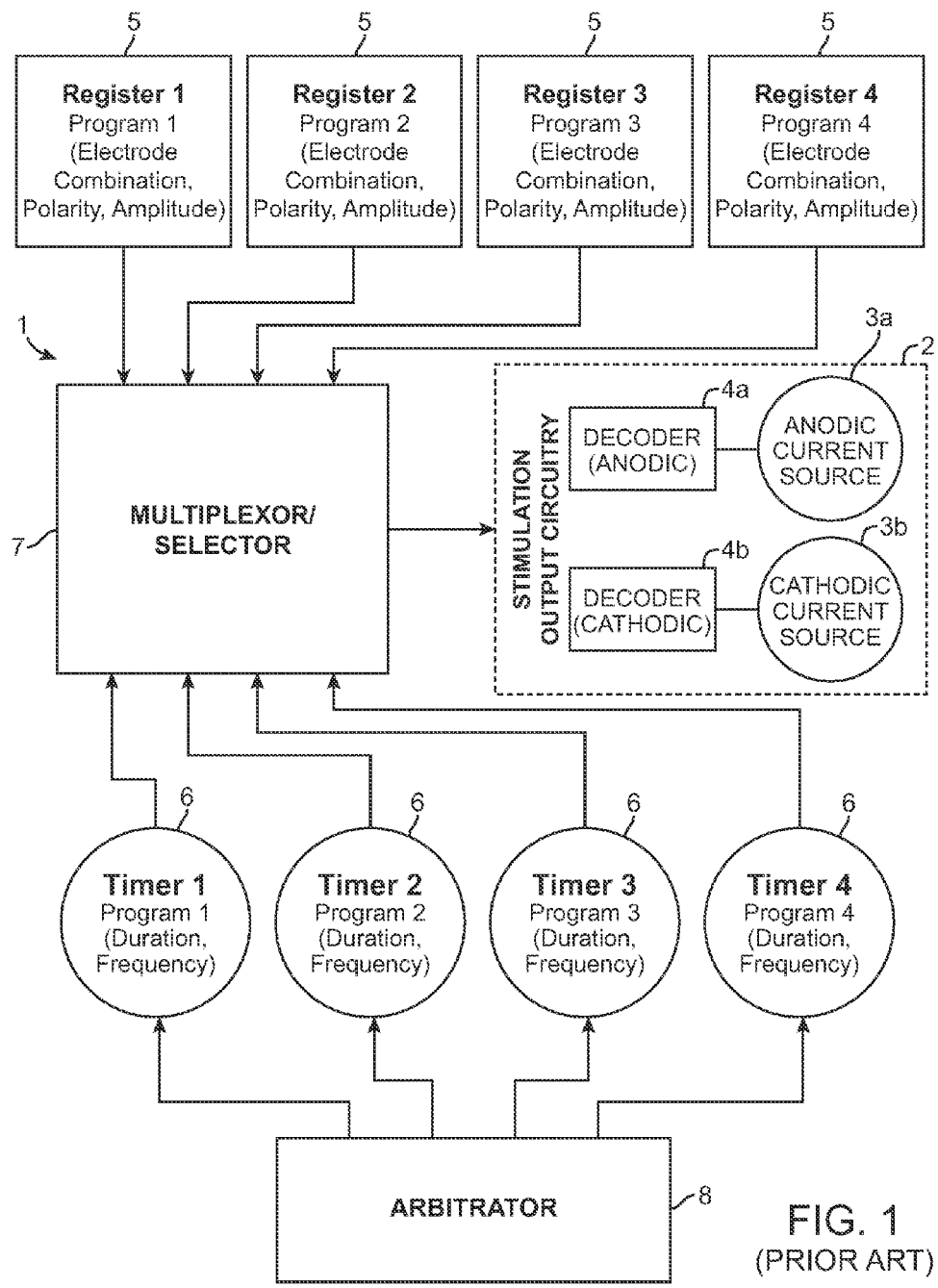
FIG. 1 is a block diagram of prior art control circuitry for preventing overlap between pulses of electrical waveforms programmed in multiple timing channels.
Figure 2:
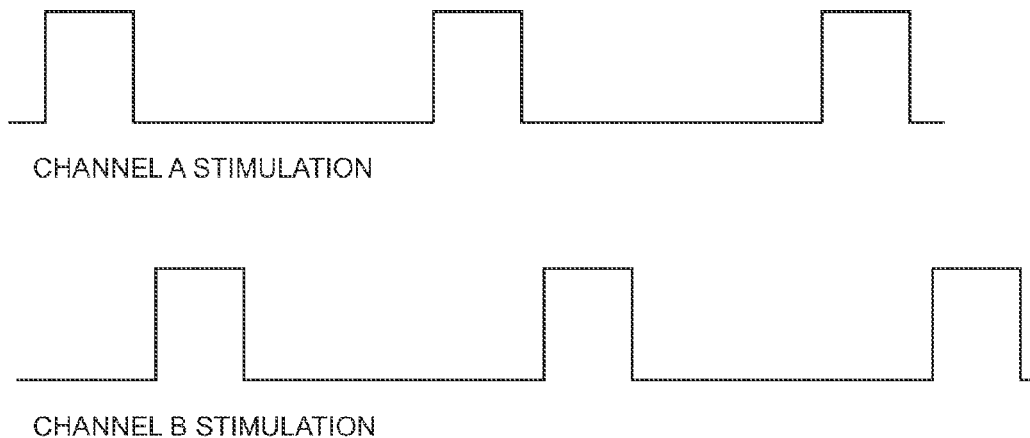
FIG. 2 is a plot illustrating two pulsed electrical waveforms generated in two timing channels by a prior art system, wherein the waveforms have the same pulse frequency, such that pulses of the waveforms do not overlap.
Figure 3:
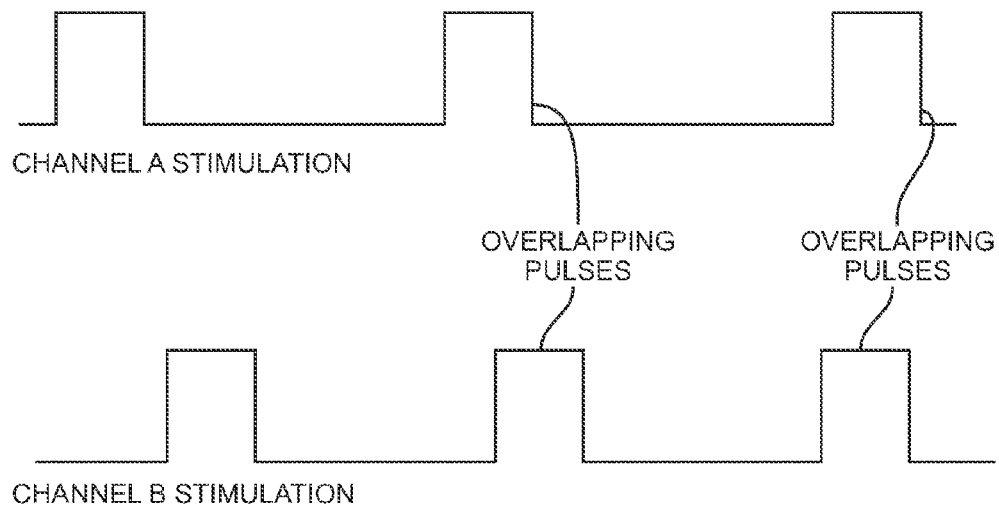
FIG. 3 is a plot illustrating two pulsed electrical waveforms generated in two timing channels by a prior art system, wherein the waveforms have different pulse frequencies, such that pulses of the waveforms overlap.
Figure 4:
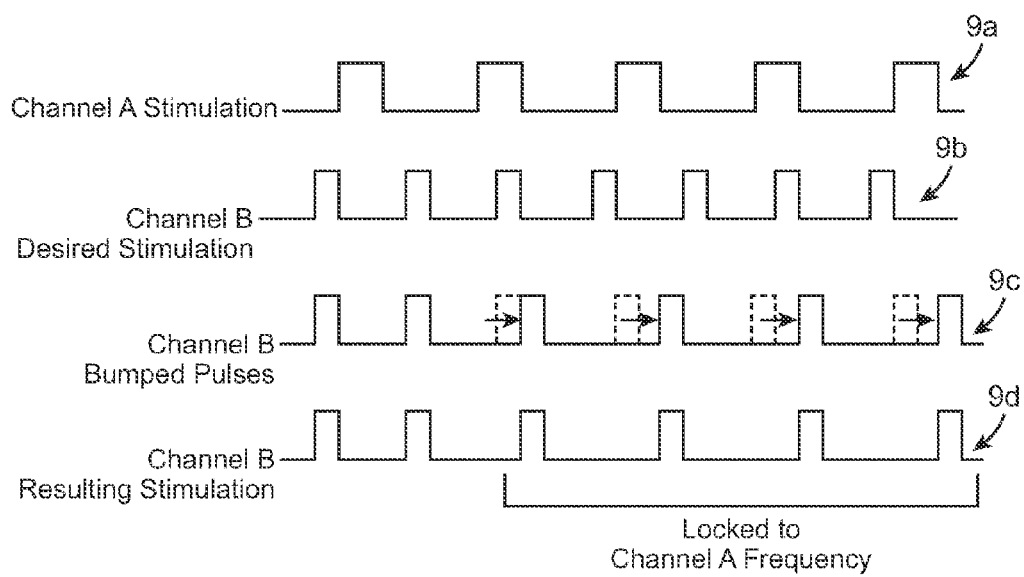
FIG. 4 is timing diagram illustrating a prior art technique for preventing the overlap between pulses of electrical pulsed waveforms programmed in multiple timing channels.
Figure 5:
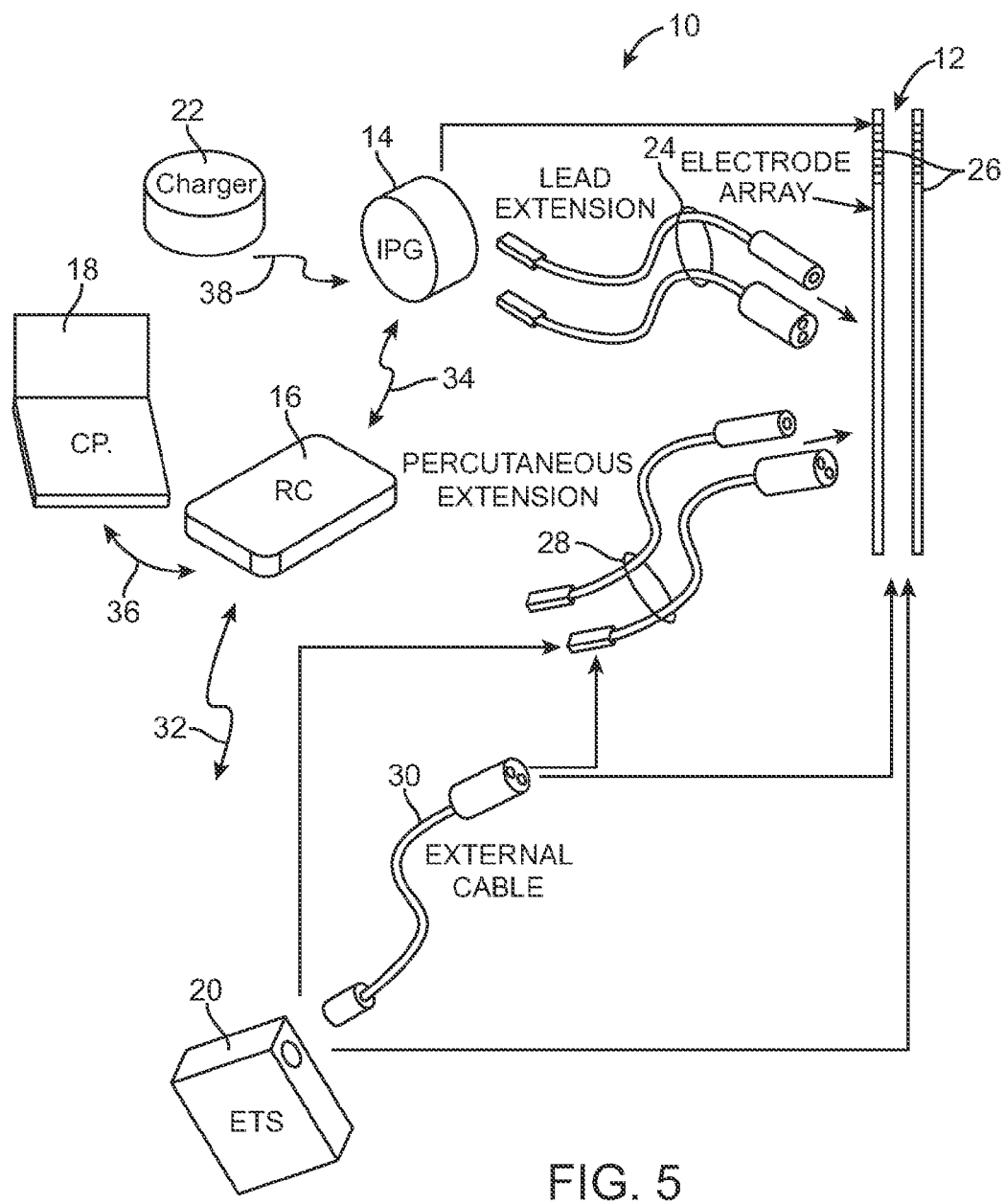
FIG. 5 is a plan view of an embodiment of a deep brain stimulation (DBS) system arranged in accordance with the present inventions.

Turning first to FIG. 5, an exemplary DBS neurostimulation system 10 generally includes one or more (in this case, two) implantable stimulation leads 12, an implantable pulse generator (IPG) 14, an external remote controller RC 16, a clinician's programmer (CP) 18, an External Trial Stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 may be arranged in-line along the stimulation leads 12. In alternative embodiments, the electrodes 26 may be arranged in a two-dimensional pattern on a single paddle lead (e.g., if cortical brain stimulation is needed). As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 6:
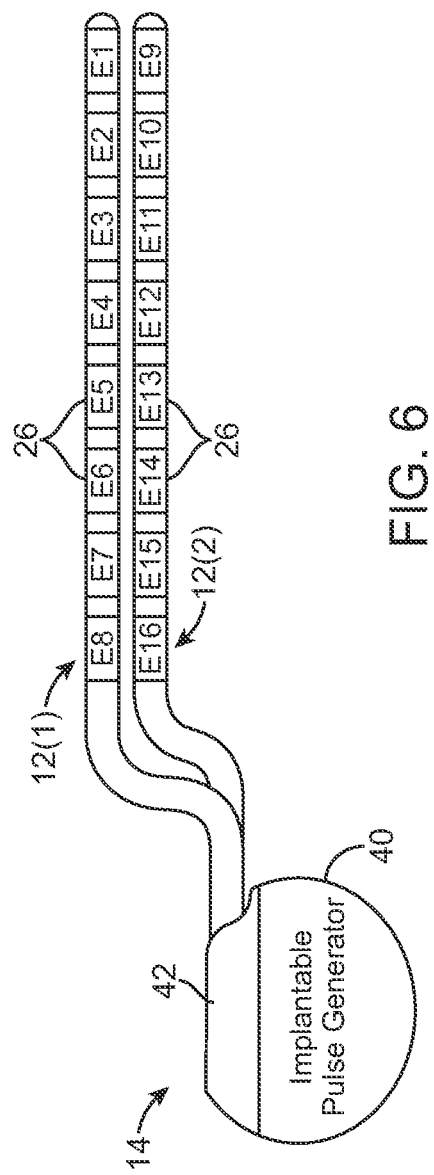
FIG. 6 is a profile view of an implantable pulse generator (IPG) and percutaneous leads used in the DBS system of FIG. 5.

Referring now to FIG. 6, the features of the stimulation leads 12 and the IPG 14 will be briefly described. One of the stimulation leads 12(1) has eight electrodes 26 (labeled E1-E8), and the other stimulation lead 12(2) has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the stimulation leads 12 mates in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and burst rate (measured as the stimulation on duration X and stimulation off duration Y).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12(1) may be activated as an anode at the same time that electrode E11 on the second lead 12(1) is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse). The recharge pulse may be active, in which case, the electrical current is actively conveyed through the electrode via current or voltage sources, or the recharge pulse may be passive, in which case, the electrical current may be passively conveyed through the electrode via redistribution of the charge flowing from coupling capacitances present in the circuit.

As will be discussed in further detail below, the IPG 14 may be programmed by the CP 18 (or alternatively the RC 16) to generate four pulsed electrical waveforms over four respective timing channels to provide treatment to the patient in which the IPG 14 is implanted. The electrode combinations assigned to the respective timing channels will typically be those that result in the treatment of four different regions in the patient. Significantly, the IPG 14 allows overlap between the electrical pulses generated in the respective timing channels.

Figure 7:
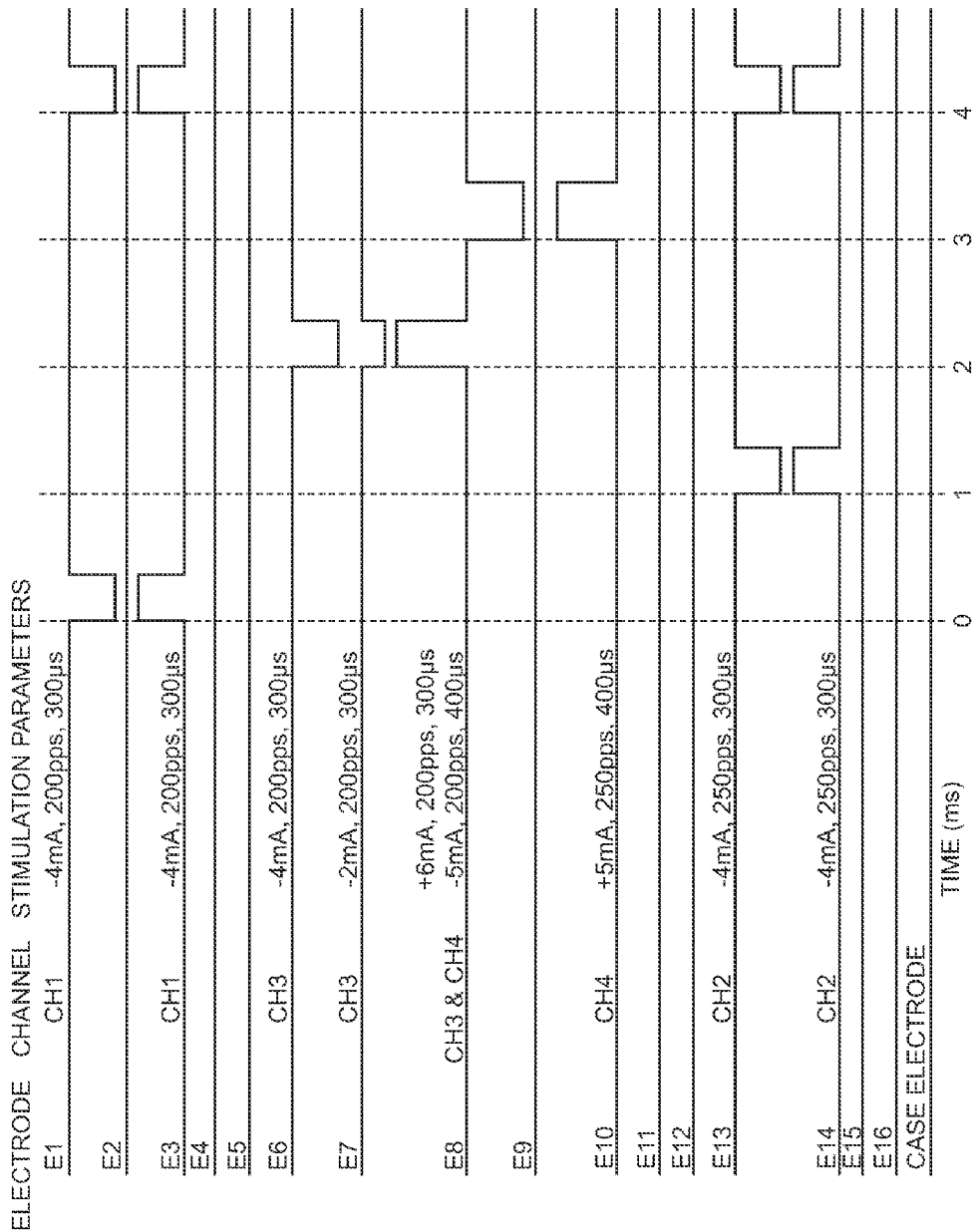
FIG. 7 is a timing diagram illustrating four exemplary pulsed electrical waveforms generated in four respective timing channels by the IPG of FIG. 6.

Referring to FIG. 7, one example of using four timing channels to simultaneously deliver pulsed electrical waveforms to groups of the electrodes E1-E16, including the case electrode, will now be described. The horizontal axis is time, divided into increments of 1 millisecond (ms), while the vertical axis represents the amplitude of a current pulse, if any applied to one of the sixteen electrodes and case electrode. Although, for purposes of simplicity, the pulsed electrical waveforms are illustrated as being monophasic in nature, it should be appreciated that the pulsed electrical waveforms may be multiphasic in nature.

At time t=0, channel 1 is set to generate and supply a current pulse having a pulse amplitude of 4 (milliamps) (mA), a pulse duration of 300 microseconds (µs), and a pulse frequency of 200 pulses per second (pps) between electrode E1 (which appears as a 4 mA anodic (positive) pulse) and E3 (which appears as a −4 mA cathodic (negative) pulse). At time t=1, channel 2 is set to generate and supply a current pulse having a pulse amplitude of 4 mA, a pulse duration of 300 µs, and a pulse frequency of 250 pps between electrode E14 (+4 mA) and E13 (−4 mA). At time t=2, channel 3 is set to generate and supply a current pulse having a pulse amplitude 6 mA, a pulse duration of 300 µs, and a pulse frequency of 200 pps between electrode E8 (+6 mA) and electrodes E6 and E7 (−4 mA and −2 mA, respectively). At t=3, channel 4 is set to generate and supply a current pulse having a pulse amplitude of 5 mA, a pulse duration of 400 µs, and a pulse frequency of 60 pps between electrodes E10 (+5 mA) and electrode E8 (−5 mA). At t=4, channel 1 is again set to generate and supply the current pulse between electrodes E1 and E3, and channel 2 is again set to generate and supply the current pulse between electrodes E14 and E13. Notably, although the pulsed electrical waveforms illustrated in FIG. 7 are monophasic in nature, the pulsed electrical waveforms delivered during a timing channel can be multiphasic in nature.

Figure 8:
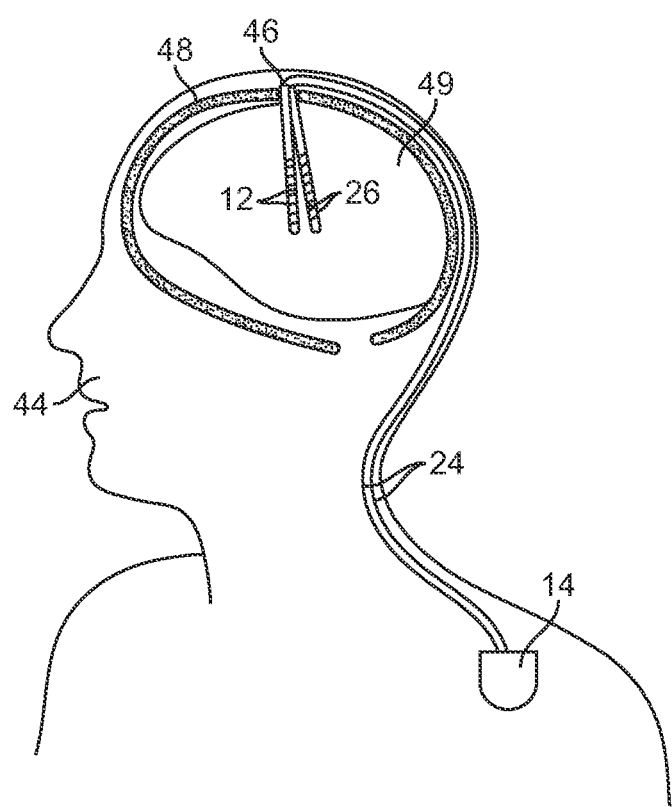
FIG. 8 is a plan view of the DBS system of FIG. 5 in use with a patient.

As shown in FIG. 8, the stimulation leads 12 are introduced through a burr hole 46 formed in the cranium 48 of a patient 44, and introduced into the parenchyma of the brain 49 of the patient 44 in a conventional manner, such that the electrodes 26 are adjacent a target tissue region whose electrical activity is the source of the dysfunction (e.g., the ventrolateral thalamus, internal segment of globus pallidus, substantia nigra pars reticulate, subthalamic nucleus, or external segment of globus pallidus). Thus, stimulation energy can be conveyed from the electrodes 26 to the target tissue region to change the status of the dysfunction. Due to the lack of space near the location where the stimulation leads 12 exit the burr hole 46, the IPG 14 is generally implanted in a surgically-made pocket either in the abdomen or above the buttocks. The IPG 14 may, of course, also be implanted in other locations of the patient's body. The lead extension(s) 24 facilitates locating the IPG 14 away from the exit point of the electrode leads 12.

Figure 9:
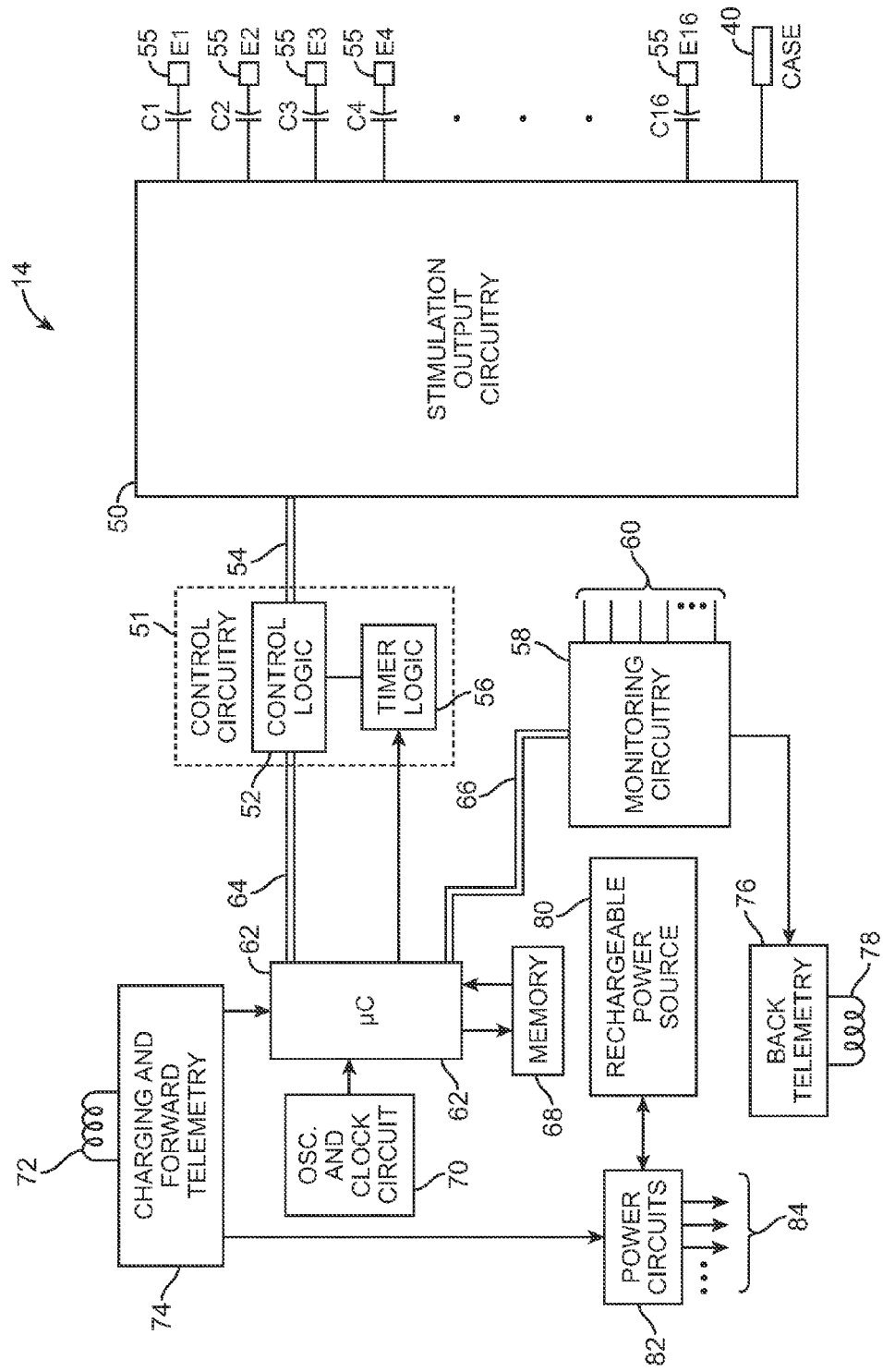
FIG. 9 is a block diagram of the internal components of the IPG of FIG. 6.

Turning next to FIG. 9, the main internal components of the IPG 14 will now be described. The IPG 14 includes stimulation output circuitry 50 configured for generating electrical stimulation energy in accordance with a defined pulsed waveform having a specified pulse amplitude, pulse rate, pulse width, pulse shape, and burst rate under control of control circuitry 51 over data bus 54. The control circuitry 51 includes control logic 52, which controls the electrodes to be activated, polarity of the active electrodes, and amplitude of the current at the active electrodes, and timer logic 56, which controls the pulse frequency and pulse width of the pulsed electrical waveform. The stimulation energy generated by the stimulation output circuitry 50 is output via capacitors C1-C16 to electrical terminals 55 corresponding to the lead electrodes 26, as well as the case electrode 40. As will be discussed in further detail below, the stimulation output circuitry 50 comprises anodic current source circuitry and cathodic current source circuitry, each of which includes at least one non-dedicated source (i.e., a source that can be temporally switched between selected ones of the lead electrodes 26 and case electrode 40).

Any of the N electrodes may be assigned to up to k possible groups or "channels." In one embodiment, k may equal four. The channel identifies which electrodes are selected to simultaneously source or sink current to create an electric field in the tissue to be stimulated. Amplitudes and polarities of electrodes on a channel may vary, e.g., as controlled by the CP 18. External programming software in the CP 18 is typically used to set stimulation parameters including electrode polarity, amplitude, pulse rate and pulse duration for the electrodes of a given channel, among other possible programmable features.

The N programmable electrodes can be programmed to have a positive (sourcing current), negative (sinking current), or off (no current) polarity in any of the k channels. Moreover, each of the N electrodes can operate in a multipolar (e.g., bipolar) mode, e.g., where two or more electrode contacts are grouped to source/sink current at the same time. Alternatively, each of the N electrodes can operate in a monopolar mode where, e.g., the electrode contacts associated with a channel are configured as cathodes (negative), and the case electrode (i.e., the IPG case) is configured as an anode (positive).

Further, the amplitude of the current pulse being sourced or sunk to or from a given electrode may be programmed to one of several discrete current levels, e.g., between 0 to 10 mA in steps of 0.1 mA. Also, the pulse duration of the current pulses is preferably adjustable in convenient increments, e.g., from 0 to 1 milliseconds (ms) in increments of 10 microseconds (µs). Similarly, the pulse rate is preferably adjustable within acceptable limits, e.g., from 0 to 1000 pulses per second (pps). Other programmable features can include slow start/end ramping, burst stimulation cycling (on for X time, off for Y time), interphase, and open or closed loop sensing modes.

Significantly, as will be described in further detail below, the control logic 52 and timer logic 56 control the stimulation output circuitry 50 in such a manner as to allow overlap between pulses in the channels despite the fact that a current source of the same polarity (either anodic or cathodic) is shared by the electrodes 26.

The IPG 14 further comprises monitoring circuitry 58 for monitoring the status of various nodes or other points 60 throughout the IPG 14, e.g., power supply voltages, temperature, battery voltage, and the like. The IPG 14 further comprises processing circuitry in the form of a microcontroller (µC) 62 that controls the control logic over data bus 64, and obtains status data from the monitoring circuitry 58 via data bus 66. The IPG 14 additionally controls the timer logic 56. The IPG 14 further comprises memory 68 and oscillator and clock circuitry 70 coupled to the microcontroller 62. The microcontroller 62, in combination with the memory 68 and oscillator and clock circuit 70, thus comprise a microprocessor system that carries out a program function in accordance with a suitable program stored in the memory 68. Alternatively, for some applications, the function provided by the microprocessor system may be carried out by a suitable state machine.

Thus, the microcontroller 62 generates the necessary control and status signals, which allow the microcontroller 62 to control the operation of the IPG 14 in accordance with a selected operating program and stimulation parameters. In controlling the operation of the IPG 14, the microcontroller 62 is able to individually generate a train of stimulus pulses at the electrodes 26 using the stimulation output circuitry 50, in combination with the control logic 52 and timer logic 56, thereby allowing each electrode 26 to be paired or grouped with other electrodes 26, including the monopolar case electrode. In accordance with stimulation parameters stored within the memory 68, the microcontroller 62 may control the polarity, amplitude, rate, pulse duration and channel through which the current stimulus pulses are provided. The microcontroller 62 also facilitates the storage of electrical parameter data (or other parameter data) measured by the monitoring circuitry 58 within memory 68, and also provides any computational capability needed to analyze the raw electrical parameter data obtained from the monitoring circuitry 58 and compute numerical values from such raw electrical parameter data.

The IPG 14 further comprises an alternating current (AC) receiving coil 72 for receiving programming data (e.g., the operating program and/or stimulation parameters) from the RC 16 (shown in FIG. 5) in an appropriate modulated carrier signal, and charging and forward telemetry circuitry 74 for demodulating the carrier signal it receives through the AC receiving coil 72 to recover the programming data, which programming data is then stored within the memory 68, or within other memory elements (not shown) distributed throughout the IPG 14.

The IPG 14 further comprises back telemetry circuitry 76 and an alternating current (AC) transmission coil 78 for sending informational data sensed through the monitoring circuitry 58 to the CP 18. The back telemetry features of the IPG 14 also allow its status to be checked. For example, when the CP 18 initiates a programming session with the IPG 14, the capacity of the battery is telemetered, so that the external programmer can calculate the estimated time to recharge. Any changes made to the current stimulus parameters are confirmed through back telemetry, thereby assuring that such changes have been correctly received and implemented within the implant system. Moreover, upon interrogation by the CP 18, all programmable settings stored within the IPG 14 may be uploaded to the CP 18.

The IPG 14 further comprises a rechargeable power source 80 and power circuits 82 for providing the operating power to the IPG 14. The rechargeable power source 80 may, e.g., comprise a lithium-ion or lithium-ion polymer battery. The rechargeable battery 80 provides an unregulated voltage to the power circuits 82. The power circuits 82, in turn, generate the various voltages 84, some of which are regulated and some of which are not, as needed by the various circuits located within the IPG 14. The rechargeable power source 80 is recharged using rectified AC power (or DC power converted from AC power through other means, e.g., efficient AC-to-DC converter circuits, also known as "inverter circuits") received by the AC receiving coil 72. To recharge the power source 80, an external charger (not shown), which generates the AC magnetic field, is placed against, or otherwise adjacent, to the patient's skin over the implanted IPG 14. The AC magnetic field emitted by the external charger induces AC currents in the AC receiving coil 72. The charging and forward telemetry circuitry 74 rectifies the AC current to produce DC current, which is used to charge the power source 80. While the AC receiving coil 72 is described as being used for both wirelessly receiving communications (e.g., programming and control data) and charging energy from the external device, it should be appreciated that the AC receiving coil 72 can be arranged as a dedicated charging coil, while another coil, such as coil 78, can be used for bi-directional telemetry.

It should be noted that the diagram of FIG. 9 is functional only, and is not intended to be limiting. Those of skill in the art, given the descriptions presented herein, should be able to readily fashion numerous types of IPG circuits, or equivalent circuits, that carry out the functions indicated and described, which functions include not only producing a stimulus current or voltage on selected groups of electrodes, but also the ability to measure electrical parameter data at an activated or non-activated electrode.

Figure 10:
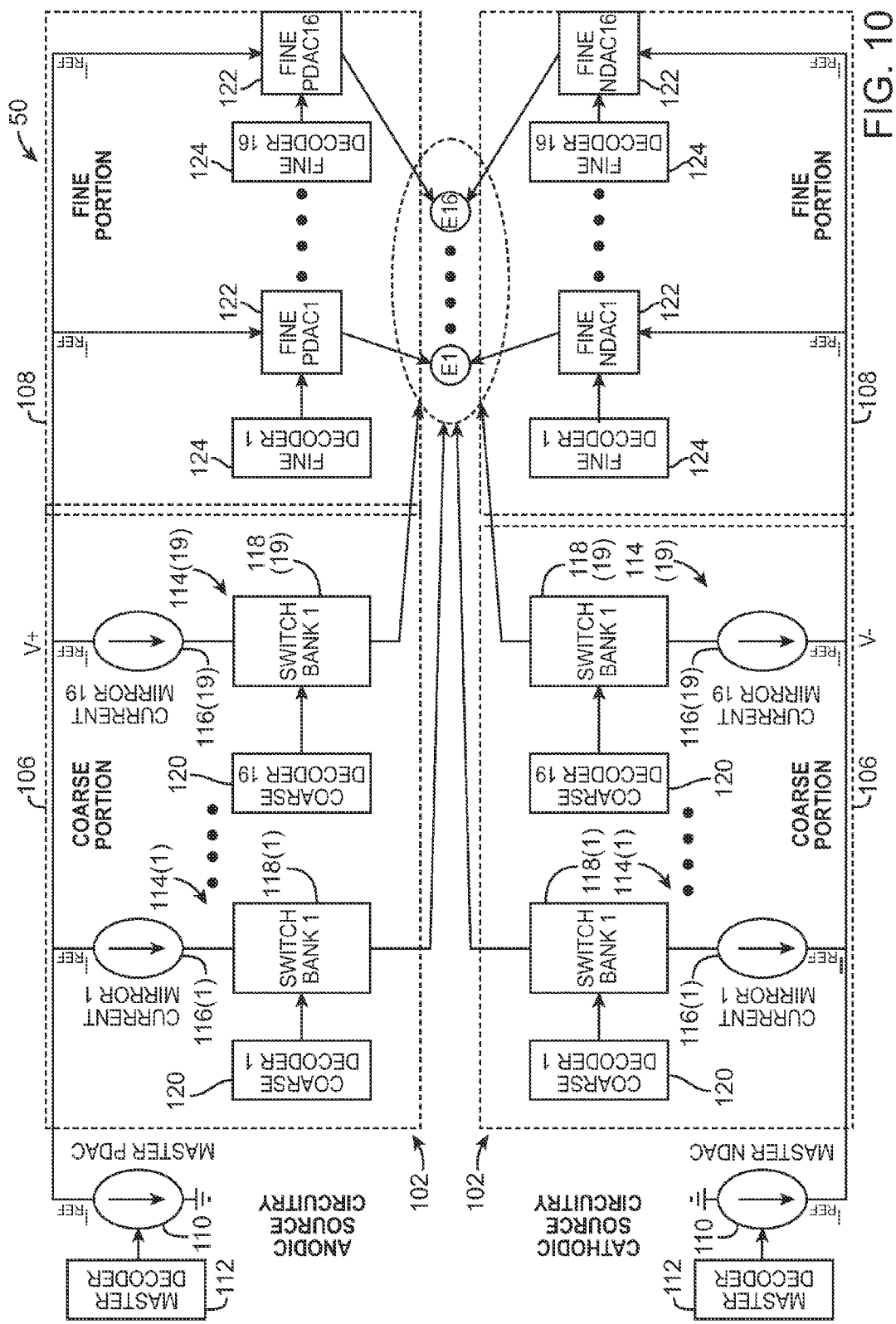
FIG. 10 is a block diagram of stimulation output circuitry contained in the IPG of FIG. 6.

Referring now to FIG. 10, the stimulation output circuitry 50 will now be described in further detail. The stimulation output circuitry 50 employs programmable anodic current source circuitry 102, and programmable cathodic current source circuitry (also known as "current sink circuitry") 104. The cathodic source circuitry 104 is similar in design and function the anodic source circuitry 102, although differing in polarity. For simplicity and to avoid redundancy, the components of the anodic current source circuitry 102 and the cathodic current source circuitry 104 are generically discussed below.

Each of the anodic and cathodic current source circuitries 102, 104 is divided into two parts: a coarse current source portion 106 and a fine current source portion 108, each of which fractionalizes the current output by the respective current source circuitries 102, 104. As its name suggests, the coarse current source portion 106 allows a coarse amount of current to be provided to a particular electrode. In other words, the amount of current that can be programmed to be sourced or sunk at a particular electrode can be adjusted in relatively large increments (e.g., 5%). By contrast, the amount of current that can be programmed to be sourced or sunk at a particular electrode by the fine current source portion 108 can be adjusted in relatively small increments (e.g., 1%).

Each of the anodic and cathodic current source circuitries 102, 104 also comprises a master reference digital-to-analog converter (DAC) 110, which generates a variable reference current $I_{ref}$ that is supplied to the coarse current source portion 106 and fine current source portion 108 of the respective current source. The master DAC 110 of the anodic current source circuitry 102 is referred to as a PDAC, and the master DAC 110 of the cathodic current source circuitry 104 is referred to as an NDAC, reflecting the fact that transistors used in anodic current sources are typically formed of P-type transistors that are biased to a high voltage (V+), whereas transistors used in cathodic current sources are typically formed of N-type transistors that are biased to a low voltage (V−).

Each master DAC 110 can comprise any structure known in the art for programming the amplification of current on the basis of a digital control signal. In the illustrated embodiment, each master DAC 110 includes eight weighted banks of current sources (not shown), and the digital control signal comprises eight bits that are respectively inputted along eight lines to the weighted banks of the master DAC 110, such that the master DAC 110 can be programmed to output $2^8=256$ different values for the reference current $I_{ref}$. In this way, the currents ultimately supplied to the coarse current source portion 106 and fine current source portion 108 can be further (and globally) varied by adjusting the gain of the master DAC 110.

The coarse current source portion 106 does not involve dedicating or hard-wiring source circuitry to each electrode. Instead, the coarse current source portion 106 is shared or distributed amongst the various electrodes via an L number of coarse current branches 114, each of which includes a current mirror 116 and an associated switch bank 118. In the exemplary case, L=19. In the illustrated embodiment, each of the current mirrors 116 outputs the same current amplitude, and in particular, a scaled version of the reference current $I_{ref}$, e.g., $5I_{ref}$. In alternative embodiments, the current output by the current mirrors 116 can be independently varied.

Notably, the current mirrors 116 are not individually adjustable in and of themselves (in contrast to the master DAC 110). Rather, the current mirrors 116 supply matched currents to the switch banks 118, with selection or not of a particular current mirror's 116 current occurring in its given switch bank 118. Each of the switch banks 118 contains an N number switches (not shown), which corresponds to the number of electrodes. In the exemplary case, N=17 (sixteen lead electrodes 26 and the case electrode). Thus, each switch bank 118 is capable of routing the current between its current mirror 116 and any of the lead electrodes E1-E16 or case electrode (not shown in FIG. 10) in response to a digital control signal. In the case of the anodic current source circuitry 102, each switch routes the current from its current mirror to any of the electrodes, and in the case of the cathodic current source circuitry 104, each switch routes the current from any of the electrodes to its current mirror.

In the illustrated embodiment, the digital control signal input into each switch bank 118 comprises seventeen bits that are respectively input along seventeen respective lines to the switches of the switch bank 118, with only one of the seventeen bits being high, thereby designating the specific switch in the respective switch bank 118 to be closed, and thus, the corresponding electrode that receives the current from the respective switch bank 118 (in the case of the anodic current source circuitry 102) or delivers the current to the respective switch bank 118 (in the case of the cathodic current source circuitry 104). Thus, only one switch per coarse current branch can be closed at one time.

It can be appreciated from this, that multiple switch banks 118 can work together to produce a current at a given electrode. For example, when operating the anodic current source circuitry 102, and assuming that each current mirror 116 supplies a current equal to $5I_{ref}$ to its respective switch bank 118, the coarse current source portion 106 can supply a maximum current of $L*I_{ref}=95I_{ref}$. If a current of $50I_{ref}$ was desired at electrode E2, the corresponding switches of any ten of the switch banks 118 can be closed, e.g., the first ten switch banks 118(1)-(10) or the last ten switch banks 118 (10)-(19). Similarly, current can be supplied to multiple electrodes at the same time. For example, suppose that $50I_{ref}$ is desired at electrode E2; $10I_{ref}$ is desired at electrode E5; and $15I_{ref}$ is desired at electrode E8. This could be achieved by closing the switches corresponding to electrode E2 (i.e., switches of ten of the switch banks (e.g., 118(1)-118(10)); closing the switches corresponding to electrode E5 of two of the switch banks (e.g., 118(11)-118(12)); and closing the switches corresponding to electrode E8 of three of the switch banks (e.g., 118(13)-118(15)).

Because each of the coarse current branches 110 outputs a current equal to $5I_{ref}$, the minimum resolution of the coarse current source portion 106 is $5I_{ref}$. Accordingly, the fine current source portion 108 additionally provides the ability to make fine adjustments to the current at the electrodes. Unlike the coarse current source portion 106, the fine current source portion 108 is preferably hard-wired to each of the electrodes 26. To the end, the fine current source portion 108 comprises a fine current DAC 122 hardwired to each of the lead electrodes E1-E16 and case electrode (not shown in FIG. 10). The fine current DAC 122 may be similar in design and architecture to the master DAC 122 used to set the reference current $I_{ref}$. Again, the fine current DAC 110 of the anodic current source circuitry 102 is referred to as a PDAC, and the fine current DAC 110 of the cathodic current source circuitry 104 is referred to as an NDAC. Each of the fine current DACs 122 receives the reference current $I_{ref}$ and outputs a variable current in increments of the reference current $I_{ref}$ in response to a digital input.

In the exemplary embodiment, each of the DACs 122 has a number J of fine current stages that can be activated in response to a digital control signal to output a variable current in a defined range, in increments of $I_{ref}$, to its respective electrode. For example, if J=5, each of the DACs 122 may supply a current ranging from $0I_{ref}$ to $5I_{ref}$ to its respective electrode. Thus, the fine current source portion 108 has a current resolution ($I_{ref}$) that is smaller than the current resolution ($5I_{ref}$) of the coarse current source portion 106. In the illustrated embodiment, the digital control signal input into each DAC 122 five bits that are respectively input along five lines into the five current stages of the respective DAC 122, such that the DAC 122 can be programmed to output 6 different scaled values ranging from $0I_{ref}$ to $5I_{ref}$.

Because of this difference in resolution, both the coarse current source portion 106 and the fine current source portion 108 can be used simultaneously to set a particular current at a given electrode. For example, assuming that it is desired to source a current of $53I_{ref}$ to electrode E2, any ten of the coarse current branches 110 can be activated to deliver $50I_{ref}$ to or from electrode E2. The fine current DAC 122 coupled to electrode E2 can be programmed to deliver an additional $3I_{ref}$ to or from electrode E2, resulting in the desired total current of $53I_{ref}$ at electrode E2.

As one skilled in the art will appreciate, it is a matter of design choice as to how many coarse current stages L are used, and how many fine current stages J are used, and these values may be subject to optimization. However if it is assumed that J fine current stages are used, then the number of coarse current stages L is preferably equal to (100/J)−1. Thus, if the number of fine current stages J is equal to 5, the number of coarse current stages L will be equal to 19, thereby allowing the coarse current source portion 106 to deliver approximately 95% of the current range to or from any electrode with a resolution of approximately 5%, and allowing the fine current source portion 108 to deliver approximately 5% of the remaining current to or from any electrode at the resolution of approximately 1%. Although it is preferred to use the same reference current $I_{ref}$ as the input to the current mirrors 116 in the coarse current source portion 106 and the DACs 122 in the fine current source portion 108, different reference currents can be used by the respective coarse current source portion 106 and fine current source portion 108. In this case, separate master DAC's may be programmed to generate different reference currents that are a scalar of each other.

In an optional embodiment, the stimulation output circuitry 50 further comprises a bank of recovery switches (not shown) respectively coupled between the electrodes and ground. In this case, a digital control signal comprising seventeen bits can be respectively input to the switches to selectively switch any of the electrodes to ground, thereby passively recovering charge at the selected electrode or electrodes.

Further disclosure discussing the details of the stimulation output circuitry 50 can be found in U.S. Patent Publication No. 2007/0100399, which is expressly incorporated herein by reference.

Figure 11:
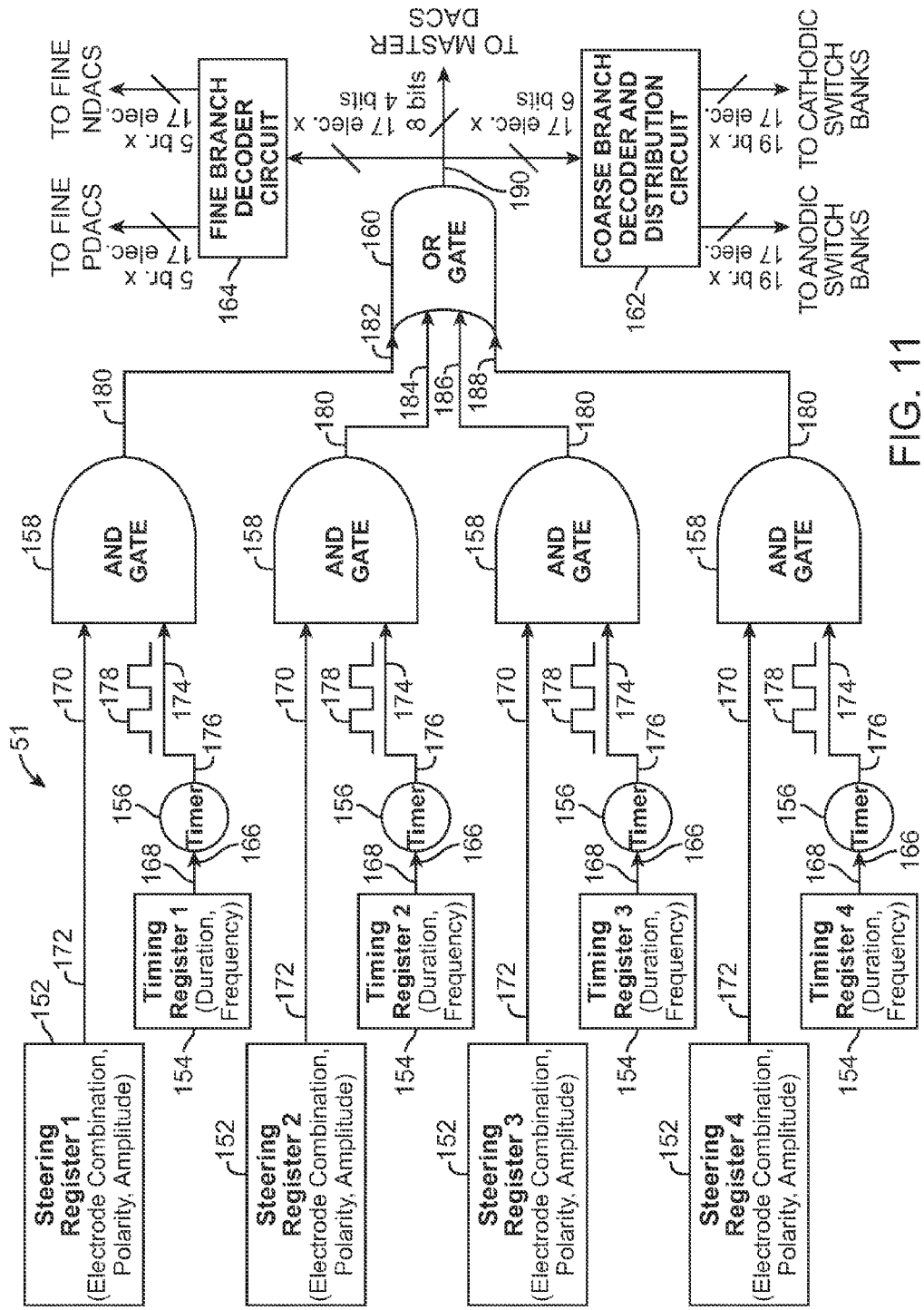
FIG. 11 is a block diagram of control circuitry contained in the IPG for defining pulsed electrical waveforms in a manner that allows overlap of pulses within respective timing channels.

Referring now to FIG. 11, control circuitry 51 (briefly discussed above with respect to FIG. 9) will be described. In response to an input of stimulation parameter sets from the microcontroller 62, the control circuitry 51 is configured for instructing the stimulation output circuitry 50 to generate and convey a plurality of pulsed electrical waveforms between the electrodes in a plurality of timing channels (e.g., as shown in FIG. 7 described above), with each pulsed electrical waveform having a pulse amplitude, pulse duration, and pulse frequency, as specified by the respective stimulation parameter set defined by the microcontroller 62.

In the illustrated embodiment, up to four pulsed electrical waveforms can be respectively generated within four timing channels. However, it should be appreciated that the number of timing channels may differ. As discussed above, the stimulation output circuitry 50 utilizes current source circuitry of different polarities (the anodic current source circuitry 102 and the cathodic current source circuitry 104) to generate each of the pulsed electrical waveforms. Although the use of both anodic current source circuitry 102 and cathodic current source circuitry 104 maximizes control of both the anodic and cathodic current amplitudes assigned to the respective electrodes, it should be appreciated that only anodic current source circuitry or only cathodic current source circuitry may be utilized. It should also be appreciated that although the stimulation output circuitry 50 utilizes current source circuitry for purposes of current steering, the stimulation output circuitry 50 may alternatively utilize voltage source circuitry.

Significantly, irrespective of whether the stimulation output circuitry 50 utilizes one or both of an anodic electrical source circuitry or cathodic electrical source circuitry (whether current or voltage), the control circuitry 51 allows the pulsed electrical waveforms to be independently generated within the respective timing channels without concern that pulses between the timing channels may overlap, and thus, without the need to manipulate the pulsed electrical waveforms in a manner that would effectively change the pulse frequencies of the pulsed electrical waveforms.

In particular, when the pulses of respective electrical waveforms generated by the stimulation output circuitry 50 will not temporally overlap each other, the control circuitry 51 instructs the stimulation output circuitry 50 to couple the anodic source circuitry 102 to different anodic sets of the electrodes and to couple the cathodic source circuitry 104 to different cathodic sets of the electrodes in a conventional manner to generate the non-overlapping pulses of the respective pulsed electrical waveforms.

For example, referring back to FIG. 7, timing channel 1 is the only channel operating at time t=0, and timing channel 2 is the only channel operating at time t=1, and therefore, the control circuitry 51 will instruct the stimulation output circuitry 50 to couple the anodic source circuitry 102 to different anodic electrode sets respectively during times t=0 and t=1 (i.e., an anodic electrode set comprising electrode E3 at t=0, and a different anodic electrode set comprising E14 at t=1), and to couple the cathodic source circuitry 104 to different cathodic electrode sets respectively during times t=0 and t=1 (i.e., a cathodic electrode set comprising electrode E1 at t=0, and a different cathodic electrode set comprising E13 at t=1). In contrast, both timing channels 1 and 2 are operated at time t=4, and therefore, the control circuitry 51 will instruct the stimulation output circuitry 50 to couple the anodic source circuitry 102 to a union of the different anodic electrode sets during time t=4 (i.e., an anodic electrode set comprising electrodes E3 and E14), and to couple the cathodic source circuitry 104 to a union of the different cathodic electrode sets during time t=4 (i.e., a cathodic electrode set comprising electrodes E1 and E13).

To this end, the control circuitry 51 generally comprises a plurality of current steering registers 152 and a plurality of timing registers 154 configured to be programmed by the microcontroller 62 in accordance with a respective plurality of stimulation parameter sets stored within the microcontroller 62. The control circuitry 51 further comprises a plurality of timers 156, each of which includes an input 166 coupled to an output 168 of a respective one of the timing registers 154. The control circuitry 51 further comprises a plurality of AND gates 158, each of which includes a first input 170 coupled to an output 172 of a respective one of the current steering registers 152, and a second input 174 coupled to an output 176 of a respective one of the timing timers 154. Because there are four timing channels, and thus, four stimulation parameter sets, the control circuitry 51 comprises four corresponding current steering registers 152, four corresponding timing registers 154, four corresponding timers 156, and four corresponding AND gates 158. Notably, although a single steering register and a single timing register may be used for each timing channel, in actuality, each register defined herein may comprise several discrete registers. For example, each electrode or a subset of electrodes may be associated with its own register. For the purposes of this specification, the term "register" may be defined as a set of discrete registers, whether such register set includes only one discrete register or a multitude of discrete registers.

For the corresponding pulsed electrical waveform to be transmitted in the corresponding timing channel, each of the current steering registers 152 stores information related to the electrodes to be activated, as well as the amplitude and polarity of the current at the active electrodes, in accordance with the corresponding stimulation parameter set stored within the microcontroller 62. For example, each current steering register 152 stores a digital representation of the set of electrodes to be activated for the respective pulsed electrical waveform to be generated during the respective timing channel. In one embodiment, the stored digital representation of the active electrode set takes the form of a plurality of binary values indicative of the relative current amplitude values to be assigned to the electrodes.

In the illustrated embodiment, each binary value defines the polarity and number of coarse current source branches and fine current source branches of the stimulation output circuitry 50 assigned to the respective electrode. In the exemplary case, a zero binary value indicates that the corresponding electrode is not to be activated, whereas a non-zero binary value indicates that the corresponding electrode is to be activated at a relative current value defined by the binary value (i.e., the number of coarse and fine current branches assigned to the electrode). In the illustrated embodiment, a polarity value of "1" indicates that the electrode is anodic, whereas a polarity value of "0" indicates that the electrode is cathodic, although it should be appreciated that a polarity binary value of "0" may indicate that the electrode is anodic, and a polarity value "1" may indicate that the electrode is anodic.

Each current steering register 152 also stores a digital global current value to be assigned to the active electrodes for the respective pulsed electrical waveform to be generated during the respective timing channel. In the illustrated embodiment, the digital global current value is indicative of the reference current $I_{ref}$ output by the master DAC 110 of the anodic current source circuitry 102 and the cathodic current source circuitry 104, which is preferably the same.

With reference to FIGS. 12a-12d, an example of the binary values stored by each of the current steering registers 152 will be described.

As there shown, for Timing Channel 1 (FIG. 12a), a coarse current binary value of 00100, a fine current binary value of 100, and a polarity binary value of 0 are assigned to electrode E1 (i.e., four coarse current branches and four fine current branches of the cathodic current source circuitry 104 are to be coupled to electrode E1), and a coarse current binary value of 00100, a fine current binary value of 100, and a polarity binary value of 1 are assigned to electrode E1 (i.e., four coarse current branches and four fine current branches of the anodic current source circuitry 102 are to be coupled to electrode E3).

For Timing Channel 2 (FIG. 12b), a coarse current binary value of 00100, a fine current binary value of 100, and a polarity binary value of 0 are assigned to electrode E13 (i.e., four coarse current branches and four fine current branches of the cathodic current source circuitry 104 are to be coupled to electrode E13), and a coarse current binary value of 00100, a fine current binary value of 100, and a polarity binary value of 1 are assigned to electrode E14 (i.e., four coarse current branches and four fine current branches of the anodic current source circuitry 102 are to be coupled to electrode E14).

For Timing Channel 3 (FIG. 12c), a coarse current binary value of 00100, a fine current binary value of 100, and a polarity binary value of 0 are assigned to electrode E6 (i.e., four coarse current branches and four fine current branches of the cathodic current source circuitry 104 are to be coupled to electrode E6), a coarse current binary value of 00010, a fine current binary value of 010, and a polarity binary value of 0 are assigned to electrode E7 (i.e., two coarse current branches and two fine current branches of the cathodic current source circuitry 104 are to be coupled to electrode E7), and a coarse current binary value of 00111, a fine current binary value of 001, and a polarity binary value of 1 are assigned to electrode E8 (i.e., seven coarse current branches and one fine current branch of the anodic current source circuitry 102 are to be coupled to electrode E8).

For Timing Channel 4 (FIG. 12d), a coarse current binary value of 00110, a fine current binary value of 000, and a polarity binary value of 0 are assigned to electrode E8 (i.e., six coarse current branches and zero fine current branches of the cathodic current source circuitry 104 are to be coupled to electrode E8), and a coarse current binary value of 00110, a fine current binary value of 000, and a polarity binary value of 1 are assigned to electrode E10 (i.e., six coarse current branches and zero fine current branches of the anodic current source circuitry 102 are to be coupled to electrode E10).

As can be seen in FIGS. 12a-12d, a coarse current binary value of 00000 and a fine current binary value of 000 are assigned to all inactive electrodes. For all of the timing channels, the digital global current value is set to be 10000000, such that half of the total anodic current and cathodic current is made available to the active electrodes by the master DAC's 110. Thus, the assignment of coarse current branches and fine current branches defines the relative current amplitudes at the active electrodes, while the setting of the master DAC's 110 ultimately defines the global current amplitude at the active electrodes.

For the corresponding pulsed electrical waveform to be transmitted in the corresponding timing channel, each of the timing registers 154 stores information related to the pulse frequency and pulse duration in accordance with the corresponding stimulation parameter set stored within the microcontroller 62.

Referring back to FIG. 11, each of the timers 156 outputs a phase enabling 178 signal in accordance with a pulse duration and pulse frequency defined by the timing information stored in the respective timing registers 154. That is, the phase enabling signal 178 output by each timer 154 will be high (i.e., logical "1") for a time equal to the duration of the pulses to be generated and at a frequency equal to the frequency of the pulses to be generated. Thus, it can be appreciated that, when the phase enabling signal 178 is high (i.e., logical "1"), the digital contents stored in the corresponding register 152 are gated to an output 180 of the AND gate 158 for a period of time equal to the pulse duration and at a frequency equal to the pulse frequency defined in the corresponding timing register 154.

The control circuitry 51 further comprises an OR gate 160 having inputs 182-188 coupled to the output 180 of each of the respective AND gates 158. Thus, any digital contents of the respective registers 152 (including the digital representations of the active electrode sets) that are gated to the respective outputs 180 of the AND gates 156 are combined at an output 190 of the OR gate 160 in a bit-wise manner (e.g., the first bit of a first set of gated digital contents is AND'd with the first bit of a second set of gated digital contents; the second bit of the first set of gated digital contents is AND'd with the second bit of the second set of gated digital contents, etc.) to create a union of the digital contents (effectively creating a union of the active electrodes sets in the respective timing channels). Notably, when the digital contents of only one of the registers 152 are currently gated to its respective AND gate 158 (i.e., no pulses will overlap), the union of the digital contents at the output 190 of the OR gate 160 will simply be the gated digital contents of that one current steering register 152. In contrast, when the digital contents of more than one of the current steering registers 152 are currently gated to their respective AND gates 156 (i.e., the pulses overlap), the union of the digital contents at the output 190 of the OR gate 160 will be the union of the multiple gated digital contents.

For example, referring back to FIG. 7, during time t=0, the union of the gated digital contents at the output 190 of the OR gate 160 will simply be the digital contents gated from the first register 152 (corresponding to timing channel 1); that is, the coarse current branch values, fine current values, and polarity values associated with electrodes E1 and E3, and during time t=1, the union of the gated digital contents at the output 190 of the OR gate 160 will simply be the digital contents gated from the second register 152 (corresponding to timing channel 2); that is, the coarse current branch values, fine current values, and polarity values associated with electrodes E13 and E14. In contrast, during time t=4, the union of the gated digital contents at the output 190 of the OR gate 160 will be the union of the digital contents gated both from the first register 152 and the second register 152, as illustrated in FIG. 13. Notably, because the global current values will presumably be the same for all of the timing channels, the union of the global current values will be identical to the global current value.

It should be noted that although only one AND gate 158 per timing channel is illustrated, there may be multiple AND gates per timing channel. For example, certain portions of the digital contents within the current steering timing registers may be respectively gated to the outputs of the multiple AND gates 158 by the phase enabling signals 178. For example, for each timing channel, the global amplitude binary values may be gated to the output of a AND gate, the coarse branch binary values and polarity value may be gated to the output of another AND gate, and the fine branch binary values may be gated to the output of still another AND gate.

By the same token, it should also be noted that although only one OR gate 160 is illustrated for all timing channels, there may be multiple OR gates for all timing channels. For example, an OR gate can be provided for each portion of the digital contents within the current steering timing registers to be combined. For example, the global amplitude binary values gated to the respective outputs of AND gates can be combined at the output of an OR gate to create a union of the global amplitude binary values, the coarse branch binary values and polarity value gated to the respective outputs of AND gates can be combined at the output of another OR gate to create a union of the coarse branch binary values and polarity values, and the fine branch binary values gated to the respective outputs of AND gates can be combined at the output of still another OR gate to create a union of the fine branch binary values.

In any event, the OR gate 160 outputs the union of the global current values, the union of the coarse branch binary values, and the union of the fine branch binary values.

The union of the global current values gated at the output 190 of the OR gate 160 is routed as a digital control signal, which includes 8 bits, along eight lines directly to each of the master DACs 110 (see FIG. 10). For example, with reference to FIG. 13, the binary control signal 10000000 will be routed to each of the master DACs 110 to deliver half of available current to or from the anodic and cathodic current source circuitries 102, 104.

The control circuitry 51 further comprises a coarse branch decoder and distribution circuit 162 that obtains the union of the coarse current branch values and polarity values gated at the output of the OR gate 160, and sends a digital control signal to the corresponding anodic and cathodic switch banks 118. In the illustrated embodiment, the coarse branch decoder and distribution circuit 162 receives 102 bits (17 electrodes×6 bits (five coarse branch bits and one polarity bit)) from the output 190 of the OR gate 160, and outputs nineteen digital control signals, each of which comprises 17 bits, along 17 lines to the respective anodic switch banks 118 (see FIG. 10), and nineteen digital control signals, each of which comprises 17 bits, along 17 lines to the respective cathodic switch banks 118 (see FIG. 10).

For example, with reference to FIG. 13, the coarse branch decoder and distribution circuit 162 will, in accordance with the coarse current branch binary value "00100" and polarity value "0" associated with electrode E1, make line 1 high and the remaining lines low for four switch banks 118 of the cathodic current source circuitry 104 to deliver current from the electrode E1 to four of the coarse current branches 114 (20% of the cathodic current); in accordance with the coarse current branch binary value "00100" and polarity value "1" associated with electrode E3, make line 3 high and the remaining lines low for four switch banks 118 of the anodic current source circuitry 102 to deliver current from four of the coarse current branches 114 to electrode E3 (20% of the anodic current); in accordance with the coarse current branch binary value "00100" and polarity value "0" associated with electrode E13, make line 13 high and the remaining lines low for four switch banks 118 of the anodic current source circuitry 102 to deliver current from four of the coarse current branches 114 to electrode E13 (20% of the anodic current); in accordance with the coarse current branch binary value "00100" and polarity value "1" associated with electrode E14, make line 14 high and the remaining lines low for four switch banks 118 of the cathodic current source circuitry 104 to deliver current from electrode E14 to four of the coarse current branches 114 (20% of the cathodic current).

The control circuitry 51 further comprises a fine branch decoder circuit 164 that obtains the union of the fine current branch values and polarity values gated at the output of the OR gate 160, and sends a digital control signal to the corresponding anodic and cathodic fine branch DACs 122. In the illustrated embodiment, the fine branch decoder circuit 164 receives 68 bits (17 electrodes×4 bits (three fine branch bits and one polarity bit)) from the output 190 of the OR gate 160, and outputs seventeen digital control signals, each of which comprises 5 bits, to the fine PDACs 122 (see FIG. 10), and seventeen digital control signals, each of which comprises 5 bits, to the fine NDACs 122 (see FIG. 10).

For example, with reference to FIG. 13, the fine branch decoder circuit 164 will, in accordance with the fine current branch binary value "100" and polarity value "0" associated with electrode E1, make lines 1-4 high and line 5 low for the fine NDAC 122 associated with electrode E1 to deliver current from electrode E1 to four of the fine current branches (4% of the cathodic current); in accordance with the fine current branch binary value "100" and polarity value "1" associated with electrode E3, make lines 1-4 high and line 5 low for the fine PDAC 122 associated with electrode E3 to deliver current from four of the fine current branches to electrode E3 (4% of the cathodic current); in accordance with the fine current branch binary value "100" and polarity value "0" associated with electrode E13, make lines 1-4 high and line 5 low for the fine NDAC 122 associated with electrode E13 to deliver current from four of the fine current branches to electrode E13 (4% of the cathodic current); and in accordance with the fine current branch binary value "100" and polarity value "1" associated with electrode E14, make lines 1-4 high and line 5 low for the fine PDAC 122 associated with electrode E14 to deliver current from electrode E14 to four of the fine current branches (4% of the cathodic current).

Notably, for each current source at any given time, each of the timing channels can use any number of the coarse current branches as long as the total number does not exceed L (i.e., the total number of coarse current branches for each current source). Thus, as long as number of coarse current branches required by the timing channels at any given time does not exceed the total number of coarse current branches available, one timing channel will not affect another timing channel. Thus, because the timing channels can be operated to simultaneously deliver pulses, the pulsed electrical waveforms can have independent frequencies.

It should also be noted that, when passive recharge pulses are utilized, the use of the currently activated electrodes in any particular timing channel can be stored in a charge recovery module (not shown) associated with the respective timing channel. The timer associated with the timing channel can enable passive recovery in the activated electrodes by enabling passive recovery switches (not shown) coupled between these electrodes and ground. During passive recovery, passive recovery signals for the electrodes can be gated on through an AND gate (not shown) by the timer and the output combined with the passive recovery signals of other timing channels through an OR gate (not shown). The passive recovery signals at the output of the OR gate can then be sent to the recovery switches. When an active pulse coincides with a charge recovery pulse, the passive recovery signals may be automatically inhibited (gated off) until the end of the active pulse. At the end of the active pulse, recovery resumes until the end of the passive recovery phase.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method, comprising:
    obtaining digital representations of electrode sets from a plurality of stimulation parameter sets;
    creating a union of the digital representations; and
    coupling electrical source circuitry to electrodes in accordance with the union of the digital representations.

2. The method of claim 1, wherein creating the union of the digital representations includes using an OR gate to create the union.

3. The method of claim 1, wherein each of the digital representations comprises a digital representation of current amplitude values, the method further comprising supplying electrical current from the electrical source circuitry to the electrodes in accordance with the current amplitude values.

4. The method of claim 1, wherein the electrical source circuitry comprises current source circuitry, wherein the current source circuitry comprises a plurality of current branches, the method further comprising selecting a current magnitude for each electrode by assigning one or more of the current branches to the respective electrode.

5. The method of claim 1, wherein the plurality of stimulation parameter sets define a plurality of pulsed electrical waveforms having different frequencies.

6. The method of claim 1, further comprising treating chronic pain by delivering pulsed electrical waveforms through the electrodes coupled to the electrical source circuitry in accordance with the union of the digital representations.

7. The method of claim 1, wherein the electrodes are implanted within an epidural space.

8. A system, comprising:
    a plurality of electrical terminals configured to be respectively coupled to a plurality of electrodes;
    stimulation output circuitry; and
    control circuitry configured to:
        access digital representations of electrode sets from a plurality of stimulation parameter sets, each of the electrode sets including at least some of the plurality of electrodes;
        create a union of the digital representations; and
        couple the stimulation output circuitry to at least some of the plurality of electrical terminals in accordance with the union of the digital representations.

9. The system of claim 8, wherein the stimulation output circuitry is configured to generate pulsed electrical waveforms in a plurality of timing channels.

10. The system of claim 9, wherein the pulsed electrical waveforms in the plurality of timing channels have different frequencies from each other.

11. The system of claim 10, wherein each timing channel identifies which electrodes are selected to simultaneously source or sink current to create an electric field in the tissue to be stimulated.

12. The system of claim 11, wherein the stimulation output circuitry includes at least one switch bank coupled between the electrical terminals and the current source circuitry.

13. The system of claim 8, wherein the stimulation output circuitry includes current source circuitry, and the digital representations include a representation of current amplitude values, the system being configured to supply electrical current from the current source circuitry in accordance with the current amplitude values.

14. The system of claim 13, wherein the current source circuitry includes a plurality of current branches, the system being configured to assign one or more of the current branches to electrode terminals to control the current magnitude for each of the electrode terminals.

15. The system of claim 8, further comprising:
    a plurality of registers configured to store the digital representations of the electrode sets;
    a plurality of timers configured to control pulse timing;
    a plurality of AND gates, each of which has an input coupled to an output of a respective one of the registers and an input coupled to an output of a respective one of the timers; and
    an OR gate having inputs coupled to respective outputs of the AND gates, and an output coupled to an input of the stimulation output circuitry.

16. The system of claim 15, wherein the current source circuitry comprises a plurality of current branches, the system further comprising a branch distribution circuit configured for assigning one or more of the current branches to each of the electrodes based on the output of the OR gate.

17. The system of claim 15, wherein the plurality of timers are configured to control both pulse duration timing and pulse frequency timing.

18. The system of claim 15, wherein the output of each of the registers is high if a pulsed waveform is to be delivered through a respective electrical terminal, and the output from the timer is high when a respective pulse in the pulsed waveform is active.

19. The system of claim 18, wherein the stimulation output circuitry is configured to generate pulsed electrical waveforms in a plurality of timing channels, and the pulsed electrical waveforms in the plurality of timing channels have different frequencies from each other.

20. The system of claim 15, wherein the timers are operated independently of each other.

* * * * *